(12) United States Patent
Beer et al.

(10) Patent No.: US 11,796,533 B2
(45) Date of Patent: Oct. 24, 2023

(54) SOLID-STATE INTEGRATED REAL-TIME OPTICAL MONITORING OF BIOCHEMICAL ASSAYS

(71) Applicant: Lawrence Livermore National Security, LLC, Livermore, CA (US)

(72) Inventors: N. Reginald Beer, Pleasanton, CA (US); Steven W. Bond, Livermore, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 51 days.

(21) Appl. No.: 17/529,249

(22) Filed: Nov. 17, 2021

(65) Prior Publication Data

US 2022/0074926 A1 Mar. 10, 2022

Related U.S. Application Data

(62) Division of application No. 16/043,808, filed on Jul. 24, 2018, now Pat. No. 11,209,423.

(51) Int. Cl.
| | |
|---|---|
| *G01N 21/63* | (2006.01) |
| *G01N 33/52* | (2006.01) |
| *B01L 3/00* | (2006.01) |
| *G01N 33/543* | (2006.01) |
| *G01N 21/64* | (2006.01) |

(Continued)

(52) U.S. Cl.
CPC ............. *G01N 33/525* (2013.01); *B01L 3/50* (2013.01); *G01N 21/64* (2013.01); *G01N 33/521* (2013.01); *G01N 33/54366* (2013.01); *B01L 2300/0609* (2013.01); *B01L 2300/0887* (2013.01); *C12Q 1/686* (2013.01); *C12Q 1/6806* (2013.01);

(Continued)

(58) Field of Classification Search
CPC .................. G01N 2201/0826; G01N 21/6452
See application file for complete search history.

(56) References Cited

U.S. PATENT DOCUMENTS

| | | |
|---|---|---|
| 5,384,656 A | 1/1995 | Schwenker |
| 2008/0081769 A1 | 4/2008 | Hassibi |
| 2020/0033328 A1 | 1/2020 | Beer et al. |

OTHER PUBLICATIONS

Chiarini, M., et al. "Integrated Mach-Zehnder micro-interferometer for gas trace remote sensing-", Proceedings of SPIE, vol. 6031, 603106, 6 pages, 2006, China.

(Continued)

*Primary Examiner* — Paul S Hyun
(74) *Attorney, Agent, or Firm* — Perkins Coie LLP (57) ABSTRACT

The disclosed technology includes a planar device for performing multiple biochemical assays at the same time, or nearly the same time. Each assay may include a biosample including a biochemical, enzyme, DNA, and/or any other biochemical or biological sample. Each assay may include one or more tags including dyes and/or other chemicals/reagents whose optical characteristics change based on chemical characteristics of the biological sample being tested. Each assay may be optically pumped to cause one or more of luminescence, phosphorescence, or fluorescence of the assay that may be detected by one or more optical detectors. For example, an assay may include two tags and a biosample. Each tag may be pumped by different wavelengths of light and may produce different wavelengths of light that is filtered and detected by one or more detectors. The pump wavelengths may be different from one another and different from the produced wavelengths.

12 Claims, 8 Drawing Sheets

(51) Int. Cl.
C12Q 1/686 (2018.01)
C12Q 1/6806 (2018.01)

(52) U.S. Cl.
CPC ........... G01N 2021/6419 (2013.01); G01N 2021/6421 (2013.01)

(56) References Cited

OTHER PUBLICATIONS

Formisano, V., et al., "The Planetary Fourier Spectrometer (PFS) onboard the European Mars Express mission", Planetary and Space Science 53, 963-974, 2005.
Griffiths, P., R., et al., "Fourier Transform Infrared Spectrometry", Wiley—Interscience Publication, 15 pages, 1942.
Guldimann, B., et al., "Focal plane array spectrometer: miniaturization effort for space optical instruments", Proc. SPIE 7930, MOEMS and Miniaturized Systems X, 79300O (Feb. 14, 2011).
Gupta, N., et al., "Hyperspectral imager, from ultraviolet to visible, with a KDP acousto-optic tunable filter", Applied Optics, vol. 43, No. 13, 8 pages, 2004.
Jovanov, V., et al., "Standing wave Spectrometer", Optics Express 426, vol. 18, No. 2, 13 pages, 2010.
Knipp, D., et al. "Silicon-Based Micro-Fourier Spectrometer", IEEE Transactions in Electron Devices, vol. 52, No. 3, 8 pages, 2005.
Le Coarer, E., et al., "Swifts: On-chip very high spectral resolution spectrometer," Proc. of SPIE vol. 10565 1056518-2, 6 pages, 2010.
Le Coarer, E., et al., "Wavelength-scale stationary-wave integrated Fourier-transform spectrometry," Nature Publishing Group, 6 pages, 2007.
Lee, "Investigation of cladding and coating stripping methods for specialty optical fibers," Optics and Lasers in Engineering, vol. 49, pp. 324-330, 2011.
Saleh, B. E. A., et al., "Fundamentals of Photonics", Wiley-Interscience Publication, 16 pages, 1994, USA.

$$780 - \beta(\lambda) = sin^{-1}\left(\frac{m\lambda}{d} - \sin(\alpha)\right)$$

810 — Containing, in a first sample holder, a biosample and one or more reagents, wherein the first sample holder is one of a plurality of sample holders, wherein each sample holder includes a different assay, wherein the first sample holder includes a first assay 820 — Heating the plurality of sample holders by a planar heater coupled to the plurality of sample holders 830 — Distributing, by an optical substrate layer coupled to the planar heater and the plurality of sample holders, one or more optical sources to provide excitation of the different assays including the first assay 840 — Filtering, by one or more filters coupled to the substrate layer, light generated by the one or more reagents in response to the excitation 850 — Detecting, by one or more detectors coupled to the optical substrate layer at the first sample holder, light emitted from the first assay, wherein each of the different assays at the plurality of sample holders emits light that is detected by one or more different detectors coupled to the optical substrate layer

FIG. 8

SOLID-STATE INTEGRATED REAL-TIME OPTICAL MONITORING OF BIOCHEMICAL ASSAYS

CROSS-REFERENCE TO RELATED APPLICATION

This application is a division of U.S. patent application Ser. No. 16/043,808 filed on Jul. 24, 2018, which is hereby incorporated by reference in its entirety.

FEDERALLY SPONSORED RESEARCH OR DEVELOPMENT

This invention was made with Government support under Contract No. DE-AC52-07NA27344 awarded by the United States Department of Energy. The Government has certain rights in the invention.

TECHNICAL FIELD

The present disclosure relates to monitoring biochemical assays.

BACKGROUND

Multiple biological and/or biochemical tests may be performed for patient diagnosis and treatment. Each test may require one or more different reagents, enzymes, or biosamples. The multiple tests may be conducted individually in serial with one test being performed after another, or in parallel with multiple tests being performed at the same time. The multiple tests may require different materials such as different reagents, different biosamples, and different test excitations such as different light sources. Some may require heating of biosamples, the reagents, and/or enzymes. Techniques and equipment are needed to reduce the size of equipment required to run multiple tests, reduce the costs, and to increase the speed of testing.

SUMMARY

In one aspect, an apparatus such as a planar biochemical device is disclosed. The device includes a plurality of sample holders arranged in a planar configuration forming a one-dimensional or a two-dimensional array, each sample holder configured for an assay comprising one or more biosamples and one or more reagents, a planar heater coupled to the plurality of sample holders, wherein the planar heater is operable to heat the plurality of sample holders, an optical substrate layer coupled to the planar heater, wherein the optical substrate layer distributes light from one or more optical sources to each of the sample holders, and an optical detection layer positioned to receive light from the plurality of sample holders, the optical detection layer including one or more optical detectors in alignment with each sample holder to detect light corresponding to each assay.

The planar biochemical device can include any of the following features in any combination. The planar biochemical device can include one or more optical filters positioned between the optical detection layer and the optical substrate, wherein each optical filter passes light of a predetermined wavelength and bandwidth and rejects light outside the predetermined wavelength and bandwidth. The planar biochemical device can include one or more diffraction gratings positioned between the optical detection layer and the optical substrate, the diffraction gratings separate different colors in the received light with little or no attenuation, and wherein the optical detection layer includes a two-dimensional array of charge-coupled optical detectors, or a two-dimensional array of complementary metal oxide semiconductor optical detectors. The optical substrate layer includes a source fiber with outcouplers at locations corresponding to each of the sample holders. The one or more biosamples and the one or more reagents are related to a polymerase chain reaction. The one or more optical sources produce light centered at at least two different wavelengths. The received light includes luminescent light resulting from a chemical reaction in a first assay. The received light includes fluorescent light resulting from excitation of a sample in a first assay. The received light includes phosphorescent light resulting from excitation of a sample in a first assay. The optical substrate layer is configured to receive light from the one or more optical sources through an optical fiber. The optical substrate layer is configured by machining or etching to accept, align, and/or self-register one or more lenses associated with the one or more biosamples. Light from the optical fiber is coupled to one or more of the plurality of sample holders through openings in the optical fiber cladding, where this cladding is removed at a plurality of predetermined locations. The openings in the optical fiber cladding have different sizes at at least two of the plurality of predetermined locations to allow different amounts light to be emitted towards at least two of the sample holders.

In another aspect, a method of processing a plurality of biosamples is disclosed. The method includes providing, in a first sample holder of a planar biosample monitoring device, a biosample and one or more reagents, wherein the first sample holder is one of a plurality of sample holders, wherein each sample holder includes a different assay, heating the plurality of sample holders by a planar heater coupled to the plurality of sample holders, distributing, by an optical substrate layer coupled to the plurality of sample holders, light from one or more optical sources to provide excitation of the different assays, filtering, by one or more filters coupled to the substrate layer, light generated by the one or more reagents in response to the excitation, and detecting, by one or more detectors coupled to the one or more filters, light emitted from the plurality of assays, wherein each of the different assays in the plurality of sample holders emits light that is detected by one or more different detectors coupled to the one or more filters.

The following features may be included in any combination. The optical substrate layer includes a source fiber with outcouplers at locations corresponding to each of the sample holders. The biosample and the one or more reagents are related to a polymerase chain reaction. The emitted light includes luminescent light resulting from a chemical reaction. The emitted light includes fluorescent light resulting from excitation of a sample in a first assay. The emitted light includes phosphorescent light resulting from excitation of a sample in a first assay.

In yet another aspect a planar biochemical apparatus is disclosed. The apparatus includes one or more sample holders including a first sample holder, wherein each sample holder includes an assay with one or more biosamples and one or more reagents, wherein the first sample holder includes a first assay, a planar heater to heat the one or more sample holders, and a planar optical assembly comprising: one or more optical sources to provide excitation to the first assay; and one or more detectors to detect light emitted from the first assay.

In yet another aspect, another planar biochemical device is disclosed. The device includes a plurality of sample holders arranged in a planar configuration forming a one-dimensional array, each sample holder configured for an assay comprising one or more biosamples and one or more reagents, a planar heater coupled to the plurality of sample holders, wherein the planar heater is operable to heat the plurality of sample holders, an optical substrate layer coupled to the planar heater, wherein the optical substrate layer distributes light from one or more optical sources to each of the sample holders, a filter layer comprising two or more filters positioned to receive light from the plurality of sample holders, wherein the optical substrate layer causes the received light from each sample holder to fall on two filters, wherein each filter is positioned to receive light from two sample holders through the optical substrate, and an optical detection layer positioned to receive light from the filter layer, the optical detection layer including two optical detectors per sample holder, wherein the two optical detectors are positioned to receive the light from the two filters associated with each assay.

The apparatus may include a plurality of sample holders including a first sample holder. Each sample holder may perform a different assay on one or more biosamples and one or more reagents, wherein the first sample holder performs a first assay. The apparatus may further include a planar heater coupled to the plurality of sample holders, wherein the planar heater heats the plurality of sample holders. The apparatus may include an optical substrate layer coupled to the planar heater. The optical substrate layer may distribute one or more optical sources to provide excitation to the different assays including the first assay. The apparatus may further include an optical detection layer coupled to the optical substrate layer. The optical detection layer may include one or more optical detectors per sample holder to detect light emitted from each assay. At least one of the optical detectors may detect light emitted from the first assay in the first sample holder. A first filter may be configured to receive light from a first sample holder, wherein a first detector from the one or more detectors is configured to receive light from the first filter. A second filter may be configured to receive light from the first sample holder, wherein a second detector from the one or more detectors is configured to receive light from the second filter In another aspect, a method of processing a plurality of biosamples is disclosed. The method may include containing, in a first sample holder, a biosample and one or more reagents. The first sample holder may be one of a plurality of sample holders and the first sample holder may include a first assay. Each sample holder may include a different assay. The method may further include heating the plurality of sample holders by a planar heater coupled to the plurality of sample holders. The method may include distributing, by an optical substrate layer coupled to the plurality of sample holders, one or more optical sources to provide excitation of the different assays including the first assay. The method may further include filtering, by one or more filters coupled to the substrate layer, light generated by the one or more reagents in response to the excitation. The method may include detecting, by one or more detectors coupled to the one or more filters, light emitted from the first assay. Each of the different assays in the plurality of sample holders may emit light that is detected by one or more different detectors coupled to the one or more filters.

In another aspect, a planar biochemical apparatus is disclosed. The apparatus may include one or more sample holders including a first sample holder. Each sample holder may include an assay with one or more biosamples and one or more reagents. The first sample holder may include a first assay. The apparatus may further include a planar heater to heat the one or more sample holders. The apparatus may include a planar optical assembly. The planar optical assembly may include one or more optical sources to provide excitation to the first assay. The planar optical assembly may further include one or more detectors to detect light emitted from the first assay.

The following features may be included in any combination. One or more optical filters may be included between the optical detection layer and the optical substrate, wherein the optical detection layer includes an array of photodetectors. One or more diffraction gratings may be included between the optical detection layer and the optical substrate, wherein the optical detection layer includes a two-dimensional array of charge-coupled optical detectors, or another two-dimensional array of complementary metal oxide semiconductor optical detectors. The optical substrate layer may include a source fiber with outcouplers at locations corresponding to each of the sample holders. The one or more biosamples and the one or more reagents may be related to a polymerase chain reaction. The planar heater may accelerate a polymerase chain reaction. The emitted light may include luminescent light, fluorescent light, and/or phosphorescent light resulting from a chemical reaction in the first assay. Light from the one or more optical sources may propagate in an optical fiber. The optical fiber may be attached to the optical substrate. Cladding around the optical fiber may be removed at a plurality of predetermined locations to cause light emission at the predetermined locations, wherein the light emission causes excitation of the assays. Different amounts of the cladding may be removed at the plurality of predetermined locations to cause the light emission from each of the predetermined locations to be approximately equal in intensity.

The above and other aspects of the disclosed technology are described in greater detail in the drawings, the description and the claims.

DETAILED DESCRIPTION

The disclosed technology includes a planar device for performing multiple biochemical assays at the same time, or nearly the same time. Each assay may include a biosample including a biochemical, enzyme, DNA, and/or any other biochemical or biological sample. Each assay may include one or more tags including dyes and/or other chemicals/reagents whose optical characteristics change based on chemical characteristics of the biological sample being tested. Each assay may be optically pumped to cause one or more of luminescence, phosphorescence, or fluorescence of the assay that may be detected by one or more optical detectors. For example, an assay may include two tags and a biosample. Each tag may be pumped by different wavelengths of light and may produce different wavelengths of light that are filtered and detected by one or more detectors. The pump wavelengths may be different from one another and different from the produced wavelengths. The planar apparatus may be compact in size and suitable for a hand held, hand carried, or smaller bioassay system.

The optical characterization of tags in a sample well (also referred to as a sample holder) may require optical pumping with one or more predetermined wavelengths, and collection of the light emitted from the tags including light generated by luminescence, phosphorescence, and/or fluorescence. The intensities of one or more wavelengths in the collected light may be determined. The apparatus may include a planar integrated optical system for bringing excitation or observation light into the sample wells and extracting, filtering, and detecting the emitted light. Multiple sample wells may be combined into the planar apparatus and each sample well may be interrogated at the same time, or nearly the same time, while maintaining a small form factor using inexpensive and manufacturable devices. Simultaneous interrogation or nearly simultaneous interrogation of two or more different tags may be performed by pumping the biosample and tags with multiple wavelengths and filtering the multiple wavelengths before being detected by one or more optical detectors.

Figure 1:
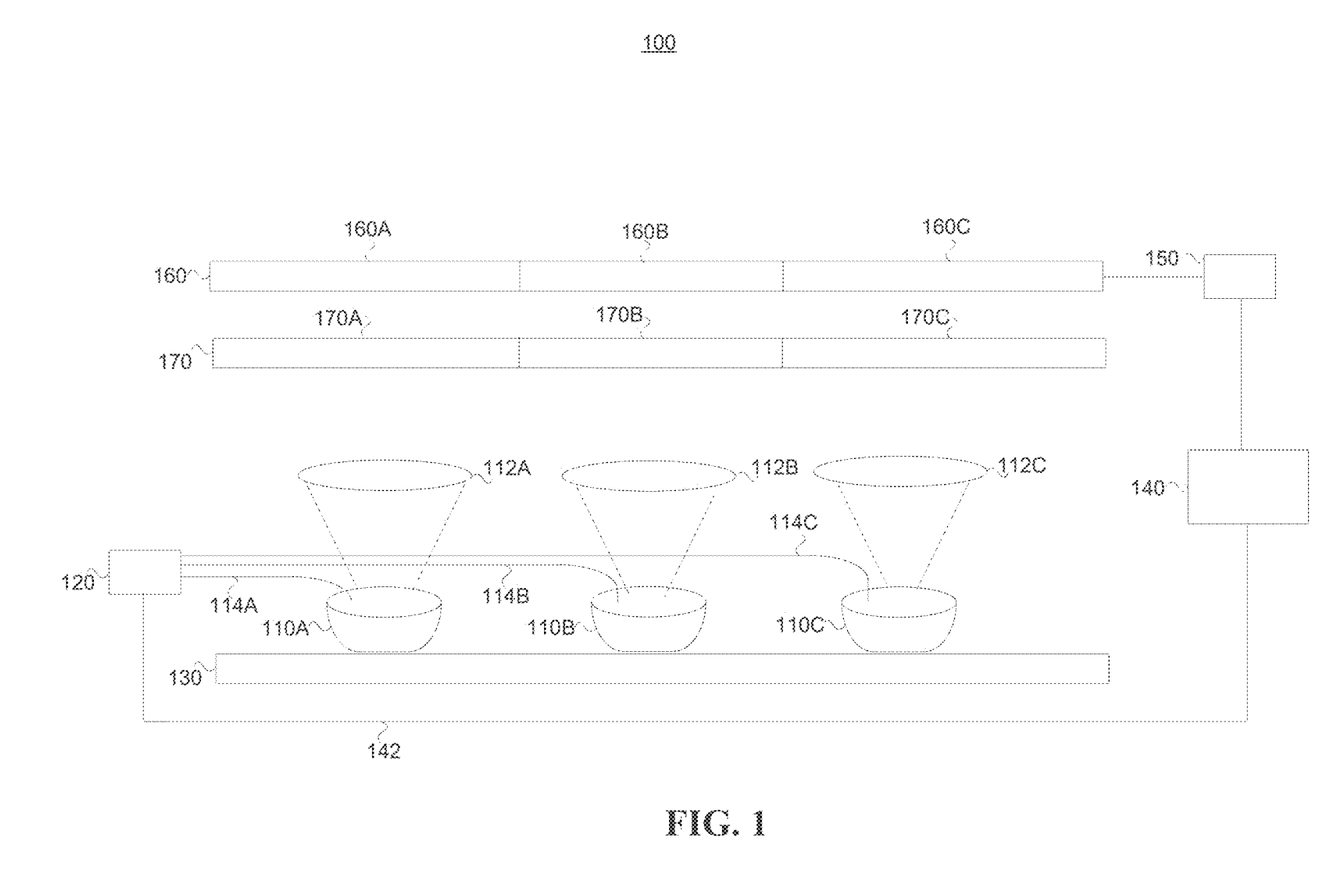
FIG. 1 depicts an example of a bioassay system, in accordance with some example embodiments.

FIG. 1 depicts an example of a bioassay system 100, in accordance with some example embodiments. In the example of FIG. 1, the bioassay system includes sample wells (or holders) 110A-110C, thermal layer 130, illuminators 114A-114C, optical source(s) 140, optical splitter 120, collection optics 112A-112C, filters 170A-170C, and detectors 160A-160C to detect fluorescent light, luminescent light, and/or phosphorescent light from one or more tags.

In the example of FIG. 1, each of the sample wells 110A, 110B, and 110C may hold one of more biosamples and/or one or more tags. The different sample wells may hold the same biosample or different biosamples. The different sample wells may include the same tags or different tags. For example, sample well 110A may include a first biosample and a phosphorescent tag, sample well 110B may include the first biosample and a luminescent tag and a fluorescent tag, and sample well 110C may include a second biosample and a phosphorescent tag, a luminescent tag, and a fluorescent tag. Although three sample wells, 110A, 110B, and 110C are shown in the example of FIG. 1, the bioassay system 100 may include any other number of sample wells, any number of biosamples, and any number of tags. The biosample wells of bioassay system 100 may be arranged in a one dimensional or a two-dimensional array configuration. For example, the bioassays may be arranged in a one-dimensional array of 10 sample wells in a row, or a two-dimensional array of six assays by six assays for a total of 36 assays.

Sample wells 110A-110C may be heated (or cooled) by thermal layer 130. For example, heating layer 130 may be in direct contact, or nearly in direct contact with sample wells 110A-110C. Heating by the thermal layer may accelerate a polymerase chain reaction (PCR) reaction in one or more of the sample wells 110A-110C. The thermal layer may be planar and may have a copper, aluminum, silicon, or other material aligned with the sample wells 110A-110C.

Illuminators 114A-114C may provide light to pump the biosamples and tags in sample wells 110A-110C. Optical splitter 120 may distribute light from optical source(s) 140 to illuminators 114A-114C. Optical source(s) 140 may provide light to optical splitter 120 via one or more optical fibers 142 (also referred to herein as source fiber 142). For example, optical source(s) 140 may include two optical sources that produce light of different wavelengths. Light form both sources may be combined and passed from 140 to optical splitter 120. Optical source(s) 140 may be switched on and off and/or the drive current adjusted as a function of time by controller 150. In the example of FIG. 1, optical splitter 120 may split the light passed along fiber 142 into three parts; one part for each illuminator 114A-114C. Optical splitter 120 may pass light of one or both wavelengths to each illuminator. For example, optical splitter 120 may pass a portion of the optical power at two wavelengths to illuminator 114A, a portion of the optical power of one wavelength to illuminator 114B, and a portion of the optical power of the other wavelength to illuminator 114C. Any other combination of wavelengths may be passed to each illuminator. Illuminators 114A-114C may cause columniation of the emitted light into the bioassays. In some example embodiments, optical splitter 120 and/or illuminators 114A-114C may include optical filters to select the wavelength(s) of light that are the sample wells. In some example embodiments, splitter 120 and illuminators 114A-114C may be combined. For example, optical splitting may be performed by optical fiber 142 with the cladding of the optical fiber removed at locations corresponding to sample wells 110A-110C. Different amounts of cladding may be removed at the different locations of the sample wells 110A-110C to cause the optical power emitted at each of the sample wells to be equal or nearly equal.

Illumination of the bioassays and tags by illuminators 114A-114C cause the tags to luminesce, fluoresce, and/or phosphoresce. The luminescent light, fluorescent light, and/or phosphorescent light may be collected by collection optics 112A-112C, passed through optical filters 170A-170C, and detected by optical detectors 160A-160C. Collection optics 112A-112C may each include one or more lenses made of glass, plastic, or other material that is optically transparent over a predetermined range of wavelengths. Collection optics 112A-112C may include other optical devices or components including coating and/or layers that may act as filters. For example, collection optics 112A may include a coating that filters the light that passes through 112A to allow collection of light over a range of wavelengths corresponding to luminescent, fluorescent and/or phosphorescent light of the tags thereby eliminating, or augmenting, filter 170A. In some example embodiments, each of the filters 170A-170C may include more than one filter. For example, filter 170A may include two filters such that a portion of the light from collection optics 112A passes through a first filter part of 170A and a second portion may pass through a second filter part in 170A. Detectors 160A-160C may include one or more detectors. Continuing the previous example, a first detector may be positioned to receive light from the first filter part in 170A and a second detector may be positioned to receive light from the second filter part in 170A. The detectors 160A-160C may detect luminescent light, fluorescent light, and/or phosphorescent light from the tags and biosamples in sample wells 110A-110C.

The multiple sample wells 110A-110C may allow simultaneous, or near simultaneous, interrogation of different luminescent, fluorescent, and/or phosphorescent tags or species. One or more of the thermal layer, the sample wells, collection optics, filters, and detectors may include alignment pins to provide for self-registration of one layer to another. In some example embodiments, the bioassay system may withstand large operating temperature swings such as between 100 degrees Celsius and 3 degrees Celsius. Other temperature swings may also be used.

Figure 2:
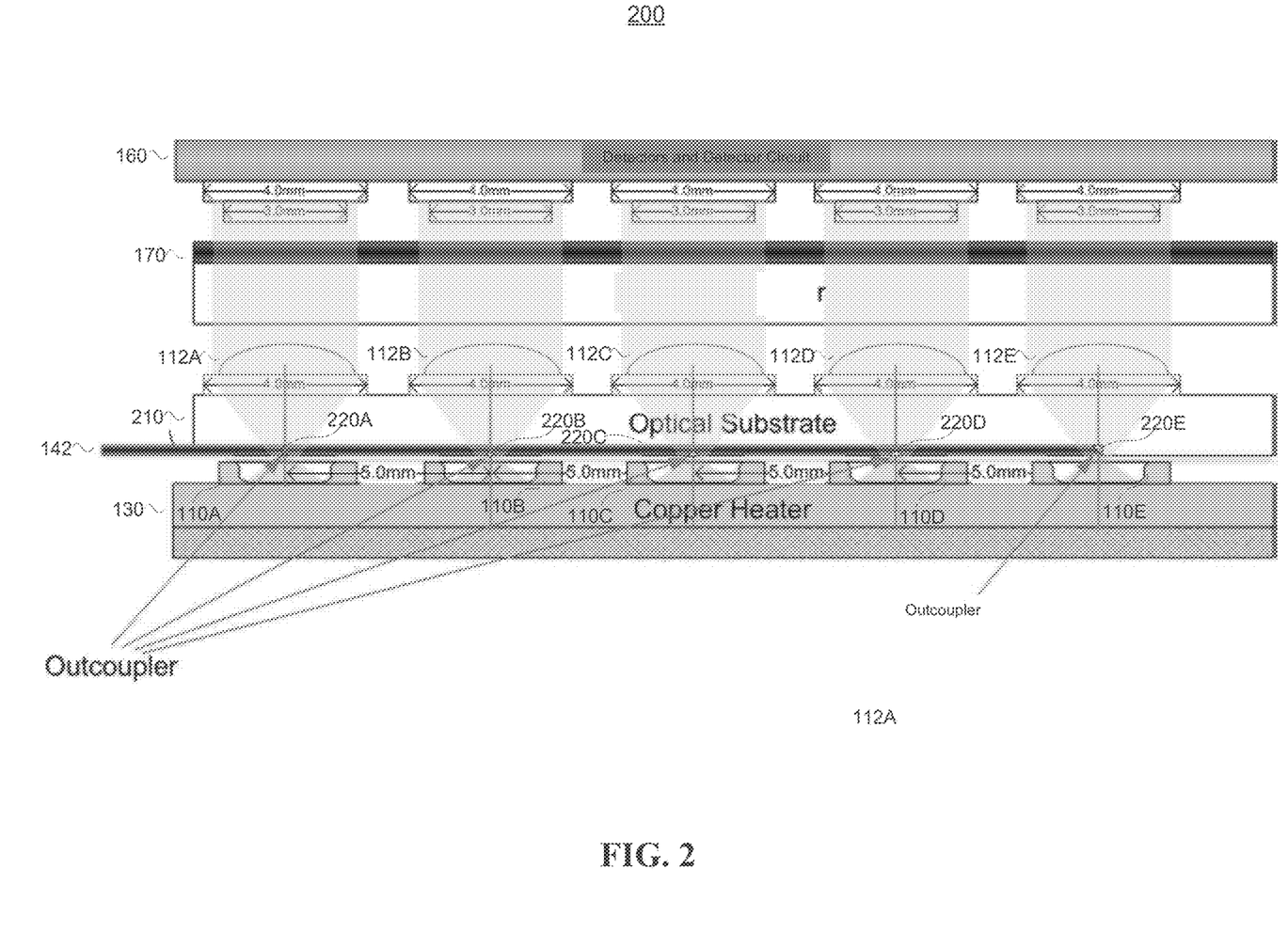
FIG. 2 depicts another example of a bioassay system, in accordance with some example embodiments.

FIG. 2 depicts an example of a bioassay system 200 showing example dimensions and materials, in accordance with some example embodiments. The description of FIG. 2 also references some of the components that were discussed in FIG. 1. FIG. 2 includes five sample wells rather than the three sample wells of FIG. 1. Bioassay system 200 includes thermal layer 130, sample wells 112A-110E, optical substrate 210, collection optics 112A-112E, filters 170 and detectors 160.

In the example of FIG. 2, sample wells 110A-110E are included as part of thermal layer 130. Sample wells 110A-110E may be made from the same material as thermal layer 130 such as copper or other material.

In the example of FIG. 2, optical substrate 210 may distribute and inject light into sample wells 110A-110E, collect any emitted luminescent, fluorescent, or phosphorescent light, and direct the emitted light toward the filters 170 and detection layer 160 including detectors 160A-160E. Detection layer 160 may include one or more detection circuits coupled to detectors 160A-160E. In some example embodiments, detection layer 160 may be combined with filter layer 170. In some example embodiments, filter layer 170 may include thin-film color filters coupled to detection layer 160. Detection layer 160 may include an array of large area photodetectors such as photodiodes. In other example embodiments, filter layer 170 may include a diffraction grating and the detection layer may include a two-dimensional array of charge coupled or complementary metal oxide semiconductor (CMOS) detectors.

In some example embodiments, large core multimode fibers may be used that have a high contrast index of refraction between the cladding and core, and high OH (hydroxyl ion) concentration. The foregoing features may aid spectral probing of fluorescent or chemiluminescent samples. The advantages of large core multimode fibers include an efficient coupling to light-emitting diodes (LEDs), multi-mode support for multi-spectral optical sources, and effective injection of light into sample wells.

Filtered LED sources used for optical source(s) 140 may produce wavelengths of light that may cause fluorescence (of phosphorescence, or luminescence) of tags used in PCR. For example one optical source may cause fluorescence of tags and dyes such as fluorescein isothiocyanate (FITC), fluorescein (FAM), and/or others. In some example embodiments, an emission filter may be coupled to an LED source to narrow the linewidth of the source and decrease the likelihood of crosstalk from the pump source light to the tag or dye generated optical signal. The emission filter may be mounted in the LED housing or may be fiber coupled. As described above, and detailed below with respect to FIG. 3, fiber 142 from optical source(s) 140 may include a plurality of outcouplers 220A-220I placed at locations corresponding to nine sample wells (not shown in FIG. 3) similar to outcouplers 220A-220E placed at locations corresponding to sample wells 110A-110E in FIG. 2. Each outcoupler 220A-220I may be implemented at least in-part by the removal of some cladding surrounding the fiber core at the locations where light emission will illuminate each of the sample wells. Outcouplers may be placed along the length of a fiber such as 142. For example, outcoupler 220A may be the closest outcoupler to optical source(s) 140 and accordingly the light intensity in fiber 142 is highest because no light has been coupled out before outcoupler 220A. Outcoupler 220A emits a portion of the light from optical source(s) 140 with the remaining portion passing further along fiber 142. The next outcoupler emits a portion of the remaining light propagating in fiber 142, and so on. In this way, each outcoupler emits a portion of the light propagating in fiber 142. Accordingly, the optical power in fiber 142 is less at each successive outcoupler from 220A to 220E. To provide equal, or nearly equal, optical power at each outcoupler 220A-220E, the pattern of removed cladding may be different at different locations to accommodate the reduced optical power at each outcoupler. In some example embodiments, the core underneath the fiber cladding may be nicked or otherwise changed to enhance light emission as described further with respect to FIG. 3.

The dimensions shown in FIG. 2 are example dimensions. In the example of FIG. 2, the lens of collection optics 112A-112E is 4 millimeters in diameter and the spacing between sample wells 110A-110E is 5 millimeters. The thermal layer 130 may be any metal or thermally conductive material. In the example of FIG. 2, the thermal layer 130 and sample wells 110A-110E are shown as copper. In other embodiments, the thermal layer may be another metal or thermally conductive material and the sample wells may be other material such as metal, thermally conductive material, or other material such as a plastic.

Figure 3:
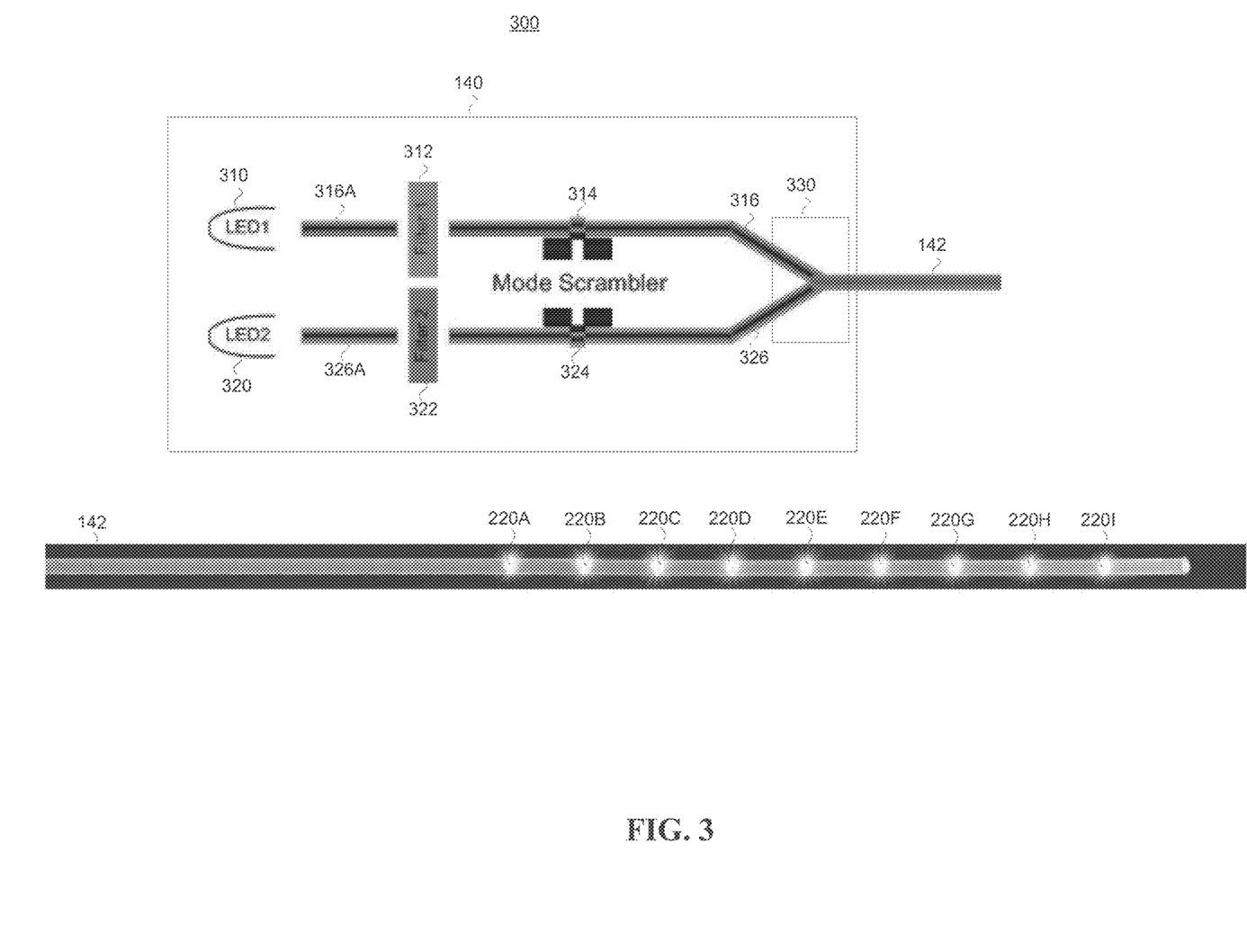
FIG. 3 depicts an example of combining multiple optical sources and examples of outcouplers, in accordance with some example embodiments.

FIG. 3 depicts an example of combining multiple optical sources and examples of outcouplers, in accordance with some example embodiments. The description of FIG. 3 also references some of the components that were described in FIGS. 1-2. Each of multiple optical sources (e.g., LEDs in FIG. 3) may be coupled to a different fiber. Each optical source may produce light at a different wavelength or range of wavelengths. The light propagating in the multiple fibers may be combined and coupled to one optical fiber. The optical fiber may be routed in a bioassay system to a plurality of sample wells. Cladding may be removed from the optical fiber to cause emission of light from the optical fiber where the cladding is removed. The core may also be changed to enhance light emission.

In the example of FIG. 3, optical source(s) 140 includes LED sources 310 and 320. LED sources 310 and 320 may produce light over different bands of wavelengths or the same band of wavelengths. LED source 310 is coupled to fiber 316A, passed through filter 312, mode scrambler 314, and provided to combiner 330. LED source 320 is coupled to fiber 326A, passed through filter 322, mode scrambler 324, and provided to combiner 330. LED sources 310 and 320 may be switched on and off and/or the drive current adjusted as a function of time by controller 150. Filters 312 and 322 may filter the LED outputs of LEDs 210 and 320 to reduce the linewidth of the light passed to mode scramblers 314 and 324 and/or to reduce optical noise, interference, and/or cross-talk between light sources. Filters 312 and 322 may pass different bands of wavelengths. Mode scramblers 314 and 324 induce mode coupling to provide a modal distribution that is independent of the optical sources 310 and 320. The mode scrambled light is provided to combiner 330 via fibers 316 and 326. Combiner 330 may combine the light carried by fibers 316 and 326 and provide the combined light to source fiber 142.

In some example embodiments, instead of source fiber 142 providing light to optical splitter 120 and illuminators 114A-114C as shown in FIG. 1, source fiber 142 may have cladding around the core removed to create illuminators or outcouplers at locations corresponding to the sample wells. The bottom section of FIG. 3 depicts an example of this configuration, where the source fiber 142 includes outcouplers 220A-220I at illustrated positions similar to outcouplers 220A-220E in FIG. 2. In some example embodiments, the core of the source fiber may be etched, scored, or material from the core otherwise removed to enhance the emission of light at the outcoupler. For example, source fiber 142 may be machined or otherwise changed at outcoupling locations along the length of the fiber to pump the samples at sample wells such as sample wells 110A-110C in FIG. 1. In some example embodiments, the outcouplers cause light emission across a broad range of wavelengths such as across the visible electromagnetic spectrum or a broader range of wavelengths. By removing the cladding of fiber 142, light is emitted from source fiber 142 into the sample wells to cause pumping of the tags/dyes. The amount of light exiting each outcoupler is adjustable by increasing the size of the outcoupler, the area of the cladding removed, and/or the depth of core removal.

The locations along source fiber 142 of the outcouplers such as outcouplers 220A-220I in FIG. 3 may be aligned with the locations of nine sample wells (not shown in FIG. 3 but similar to sample wells 110A-110E in FIG. 2). In the example of FIG. 2, the locations of outcouplers 220A-220E are aligned with sample wells 110A-110E. In some example embodiments, the cladding of fiber 142 and optionally the core may be etched after source fiber 142 has been attached or affixed to an optical substrate such as substrate 210 in FIG. 2. For example, source fiber 142 may be attached with epoxy glue into a machined recess matching the diameter of source fiber 142. The cladding may be selectively removed using either masking and etching, a mechanical machining process, or by computer controlled laser ablation. The locations of the outcouplers may be controlled using alignment features machined into the substrate 210. In some example embodiments, the source fiber may be coupled to a planar waveguide in optical substrate 210 where outcouplers are created. Planar waveguide structures may include silicon dioxide on silica, photo sensitive polymer waveguides, or injection molding. In some example embodiments, the optical substrate 210 may be machined to include alignment pins, vertical standoffs, recesses for collection optics, and troughs for waveguide and/or source fiber registration.

As described above, as light travels down source fiber 142, the light is attenuated by the successive outcouplers. Accordingly, the light provided to the "downstream" wells (closer to the end of source fiber 142 at the last sample well) to have lower optical intensity than upstream outcouplers. The amount of cladding removed at the successive outcouplers may be adjusted to compensate for this reduced light intensity to cause a nearly uniform light emission at each outcoupler along the source fiber 142. In other embodiments, the pattern of the cladding removal at the outcouplers may be uniform but the depth of an etching into the cladding may be different. In other embodiments, the pattern of cladding removal and the etch depth may be the same or nearly the same, but a surface coating may be applied to inhibit light emission out of the source fiber 142 into one or more sample wells.

Figure 4:
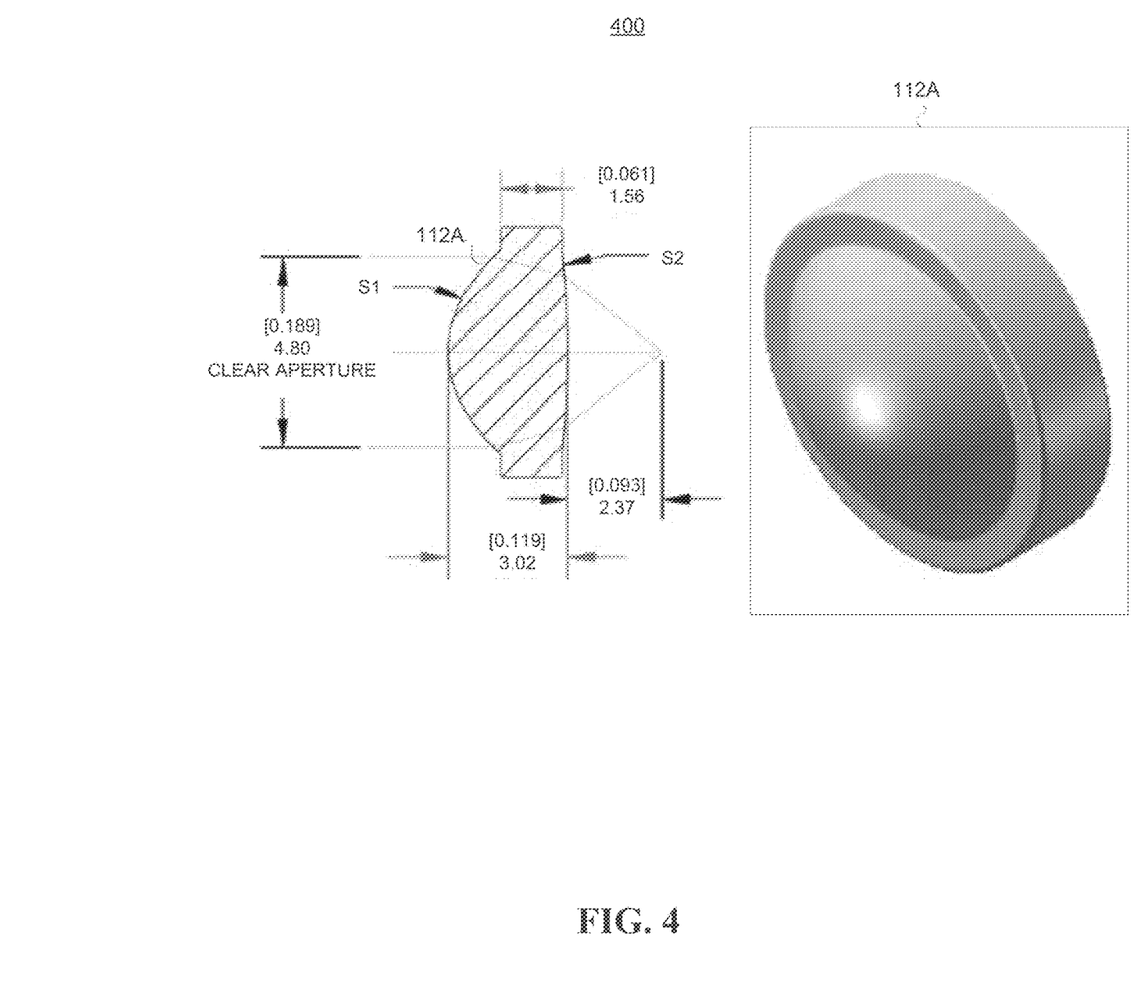
FIG. 4 depicts an example of collection optics, in accordance with some example embodiments.

FIG. 4 depicts an example of collection optics, in accordance with some example embodiments. The description of FIG. 4 also references some of the components described in FIGS. 1-3. In some example embodiments such as the bioassay system in FIG. 2, substrate 210 may be machined to register and hold in place one or more optical devices for collection optics such as collection optics 112A-112E. The collection optics may couple light from sample wells 110A-110E into optical filters 170 and detectors 160. For example, each collection optics 112A-112E may include a lens such as the example lens shown in FIG. 4. Light generated in the sample wells 110A-110E may radiate omni-directionally. In some example embodiments, the thermal layer 130 and/or sample wells 110A-110E in FIG. 2 may be reflective. For example, the sample wells may be made from a reflective material or metallic or reflective inserts may be included to reflect light from the edges of the sample well toward the top surface and collection optics for each sample well. The light may propagate through the optical substrate 210 and may be collected by the collection optics 112A-112E. In some example embodiments, a portion of the light reflected from each sample well may be blocked by the source fiber 142 and outcouplers, but because the source fiber has a small area compared to the to the area of the top surface of each sample well, the proportion of the emitted light that is blocked is insignificant. In some example embodiments, optical substrate 210 may be machined to accept, align, and/or self-register collection optics 112 including lens 112A. The machining may hold a lens such as lens 112A at a position to image a sample well onto an optical detector. As used above, machining may include one or more of machining via mechanical devices, chemical machining, etching, photolithography, or any other method of selectively causing material to be removed from a substrate such as optical substrate 210. In some example embodiments, the optical substrate, alignment features, recesses, and/or lens, may be fabricated using a rapid prototyping and/or injection molding.

FIG. 4 depicts some example sizes and distances. In the example of FIG. 4, the lens as part of collection optics 112A has clear aperture of 4.8 millimeters, the thickness is 3.02 millimeters, and the lens has a focal length of 2.37 millimeters. Other sizes, distances, and focal lengths may also be used.

Figure 5:
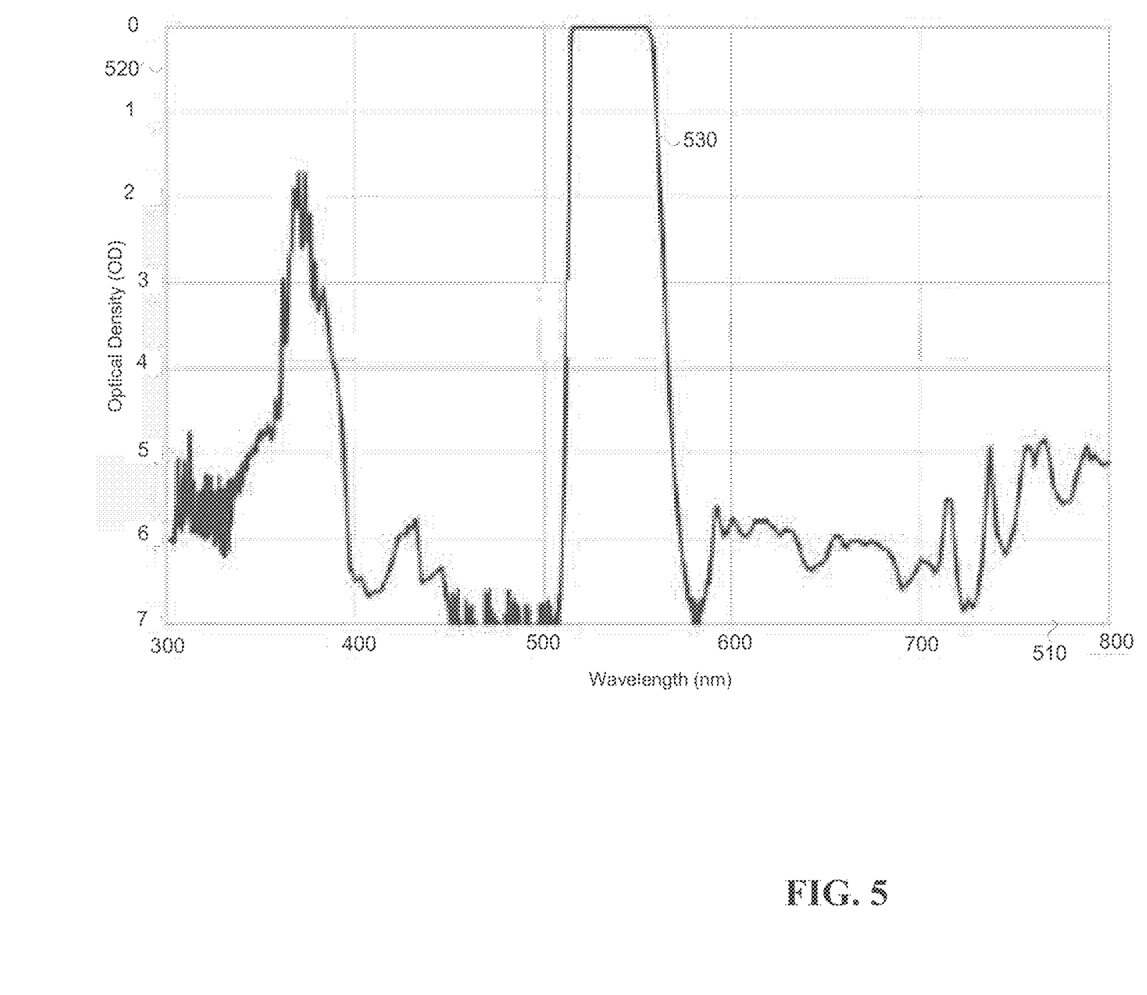
FIG. 5 depicts an example of a plot of wavelength vs. optical density for an example optical filter, in accordance with some example embodiments.

FIG. 5 depicts an example of a plot of wavelength vs. optical density for an example optical filter, in accordance with some example embodiments. Example plot 500 plots wavelength in nanometers verses optical density for a particular optical filter such as one or more of optical filters 170A-170C in FIG. 1. The plotted transmissivity curve 530 shows a peak optical density between approximately 510 nanometers and 580 nanometers. The transmissivity plot shown in FIG. 5 is illustrative. Other transmissivity characteristics may also be used. Filters consistent with the disclosed subject matter may have wider or narrower linewidths and may be centered at longer or shorter wavelengths than depicted in FIG. 5.

Figure 6:
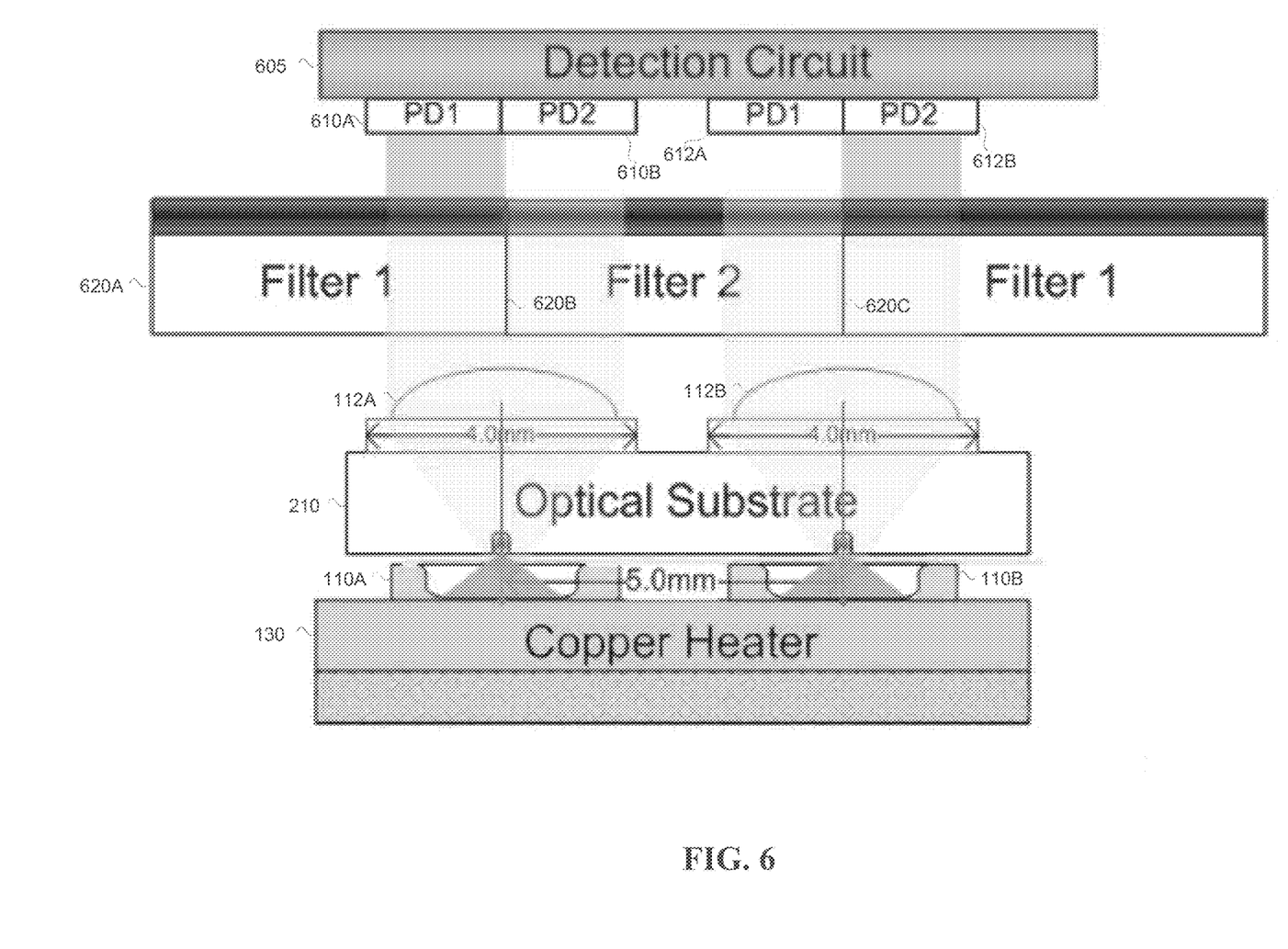
FIG. 6 depicts an example of bioassays with two optical filters and two detectors per bioassay, in accordance with some example embodiments.

FIG. 6 depicts an example of bioassays with two optical filters and two detectors per bioassay, in accordance with some example embodiments. The description of FIG. 6 also references some of the components described in FIGS. 1-5. FIG. 6 depicts a thermal layer 130 including, or coupled to, sample wells 110A and 110B, optical substrate 210 coupled to thermal layer 130 and collection optics 112A and 112B. Source fiber including outcouplers (not shown) may be placed to emit light into sample wells 110A and 110B. Collection optics 112A and 112B focus luminescent, phosphorescent, and/or fluorescent light onto detectors 610A-610B and 612A-612B from the tags and biosamples in sample wells 110A-110B.

In the example of FIG. 6, collection optics 112A is aligned to focus light on detectors 610A and 610B. Between the collection optics 112A and detectors 610A-610B are filters 620A-620B. Filter 620A is aligned to be illuminated by half or another portion of the light from collection optics 1112A. Filter 610B is aligned to be illuminated by the other half or another portion of the light from collection optics 112A. The light incident on detector 610A passes through filter 620A and the light on detector 610B passes through filter 620B. Collection optics 112B is aligned to direct the light through filter 620B and 620C to illuminate detectors 612A and 612B in a similar fashion. In this way, light from multiple tags or dyes may detected from one sample well at the same time or nearly the same time without changing samples, sources or filters.

The bioassays shown in FIG. 6 enable detection of light from multiple tags at the same time or nearly the same time. The sample wells such as 112A and 112B may be pumped by multiple wavelengths corresponding to multiple tags at the same time. In the example of FIG. 6, each of two tags at each well location may be pumped by a source producing a predetermined wavelength. Light from both sources may be carried by a source fiber and emitted into sample wells 110A-10B. A first tag may be pumped by the first wavelength carried by the source fiber, and a second tag may be pumped by the second source carried by the source fiber. The first tag may generate luminescent, phosphorescent, and/or fluorescent light that passes through 620A but not through filter 620B and is detected by detector 610A. The second tag may generate luminescent, phosphorescent, and/or fluorescent light that passes through 620B but not through filter 620A, and is detected by detector 610B.

A detection layer such as detection layer 160 included in FIG. 6 may include detectors 610A-610B and 612A-612B, and detection circuit 605. Detectors 610A-610B and 612A-612B may include an array of photodetectors mounted to a surface. For example, photo detectors may be located on a circuit board of the detection circuit 605 and aligned to be in position to receive light as described above. The circuit board may include on-board low-noise amplifiers and/or other electronics. In the example of FIG. 6, each sample well location includes two photodetectors to sample the light from two tags. In some example embodiments, the two light sources that produce the two different pump wavelengths may be pulsed at the same time or at different times. Pulsing of the light sources, such as pulsing the sources at different times or at different frequencies may facilitate electronic filtering and cross-talk reduction. Lock-in techniques may reduce noise and/or interference. In some implementations, when a sample well contains two tags, each tag may be pumped and/or a corresponding detector read at different times.

In some example embodiments, one or more diffraction gratings may replace one or more of the filters. A diffraction grating may separate colors with no, or little, attenuation of light intensity. A diffraction grating may reduce backscatter of rejected light. A diffraction grating may have a predetermined number of grating lines per unit length and may have a certain thickness. For example, a diffraction grating may have 1200 lines per millimeter and be 3 millimeters thick. In some example embodiments, a diffraction grating with 1200 lines per millimeter may provide spectral dispersion to allow a linear or two-dimensional array of detectors to separate the light from tags and to discriminate against any unconverted pump light reaching the detectors. Diffraction gratings may provide good sensitivity due to their low insertion loss, background rejection, pump segregation, fluctuation removal, and stable fluorescent dye characterization.

Figure 7:
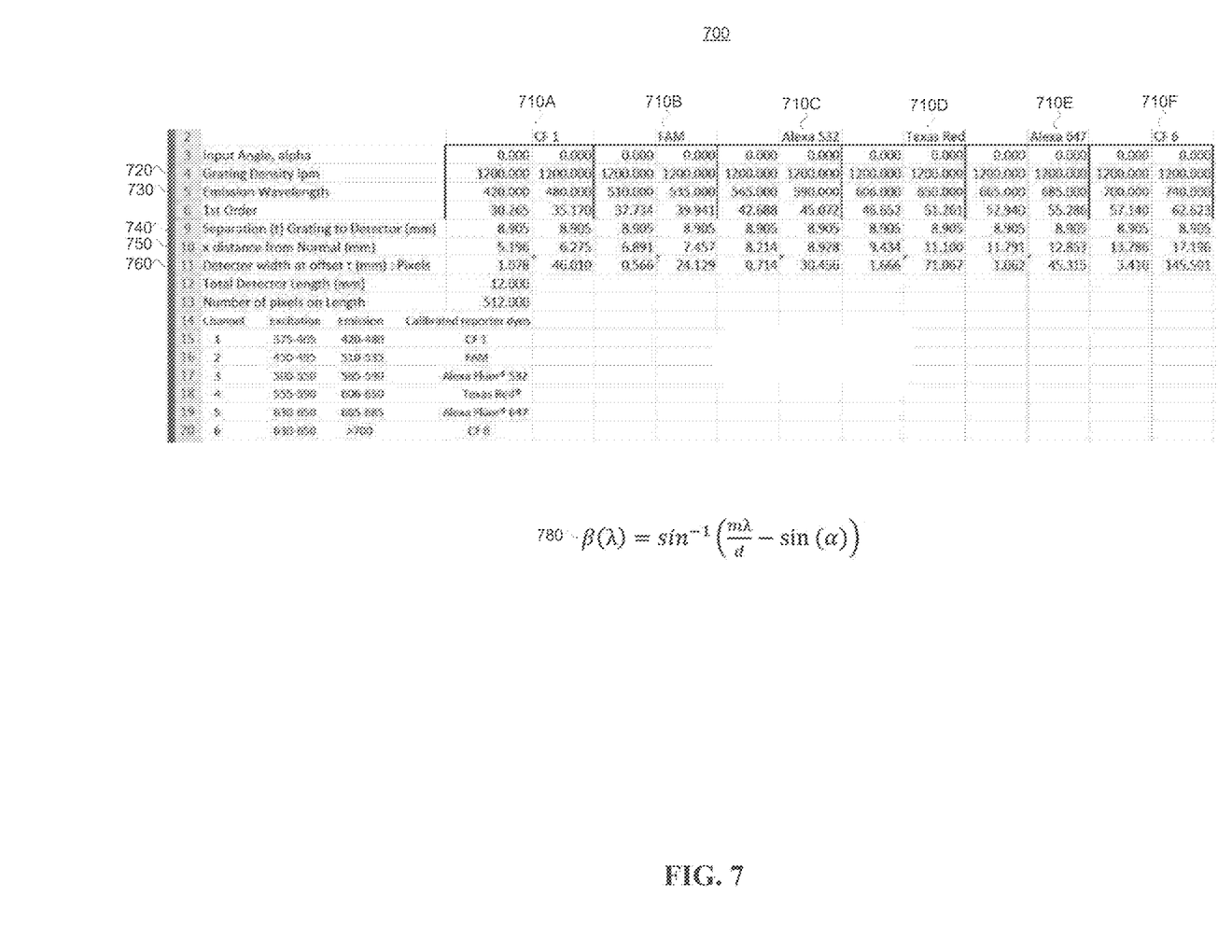
FIG. 7 depicts an example of parameter values for various dyes using a diffraction grating with 1200 lines per millimeter, in accordance with some example embodiments.

FIG. 7 depicts an example set of parameter values associated with a diffraction grating configuration that uses various dyes, in accordance with some example embodiments. The example diffraction grating has 1200 lines per millimeter. FIG. 7 includes six fluorescent dyes as examples. Other dyes may be used as well. The disclosed subject matter supports any dye.

The dyes included in FIG. 7 include: CF 1 at 710A, FAM at 710B, Alexa Fluor 532 at 710C, Texas Red at 710D, Alexa Fluor 647 at 710E, and CF 6 at 710F. The table shown in FIG. 7 shows two columns for each dye including minimum and maximum emission wavelengths. The grating equation 780 may be used to calculate the first order diffracted angle. The grating equation may then be solved to obtain a single stand-off distance "Separation (t) Grating to Detector (mm)" of 8.9 mm at 740. This distance may be chosen to give a dispersion distance to allow a linear detector array to have a sufficient number of non-overlapping pixels for detection of the individual emission wavelengths of the selected dyes.

The calculation of the "x distance from Normal (mm)" at 750 is the linear distance at the detector plane (a plane made by the top surfaces of the detectors at 160) illuminated by a specific dye. The difference between the high and low wavelength locations on the detector plane is used to calculate the "Detector width at offset t (mm)" at 760. The adjacent column illustrates the number of illuminated pixels when a 12 mm linear detector array is used with 512 pixels. Illuminated pixels shown in row 760 indicate that the FAM tag has the minimum number of adjacent active pixels at 24 pixels for the 8.9 mm standoff.

A one-dimensional array or a two-dimensional array may process electrical signals from the individual pixels. For example, the processing may sum the appropriate detector signals, gate the detector signals in time using lock-in techniques, and time average the signals to reduce noise. The "image" of the sample may be a "spectral spread" with each region being indicative of an individual light signature from a tag. The second dimension of the detector array may allow additional parallel rows of sample wells.

The foregoing large area detector and diffraction grating may be tolerant of some optical issues that may occur in the propagation path. For example, the pump light that reflects back into the detector plane may be at a different spatial location than the generated fluorescent light. Also, ineffective collimation at the collection optics may broaden the receive spot as rays impinge upon the diffraction grating at different angles.

Automated calibration and background rejection schemes can be accommodated by using the pump, diffraction, and detector plane during periods when the temperature and resulting chain reactions are not active. For example, off-cycle calibrations of the pump light location and intensity can be measured.

Furthermore, for cyclic processes such as PCR amplification monitoring, fluorescence fluctuations can be removed by n-cycle moving average computation from cycle to cycle to smooth out fluctuations and noise within individual wells cycle to cycle. The emitted signal in PCR may be exponential. Once the signal passes above a threshold of a detector, fluctuations become less of an issue in terms of assessing target presence and concentration via qPCR analysis.

Offsets or errors due to well-to-well variability and variability of sample well alignment may be reduced using background subtraction and normalization for each well to enable repeatable and accurate fluorescence intensity change measurements using standard normalization and background subtraction techniques.

Figure 8:
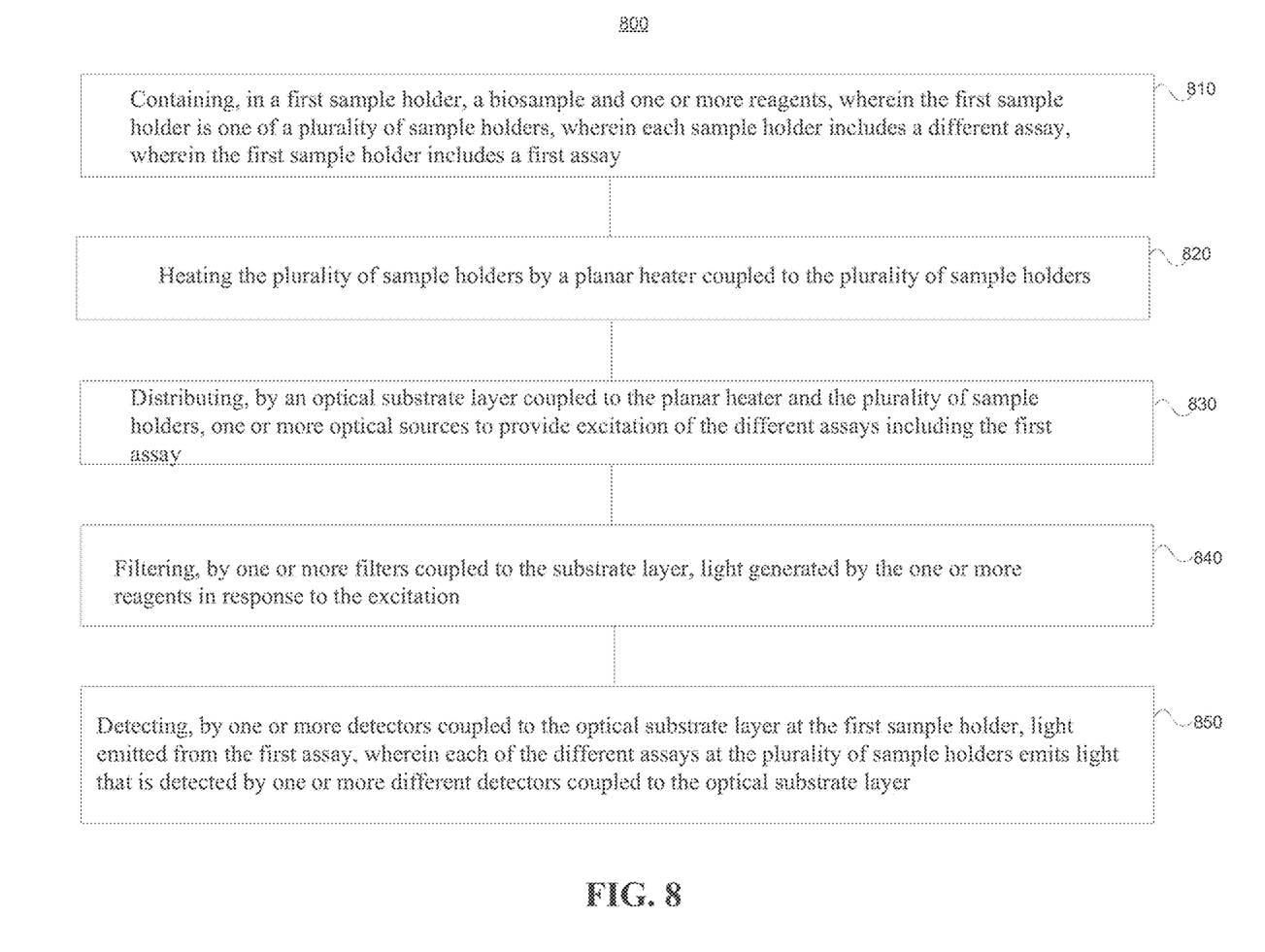
FIG. 8 depicts an example of a process, in accordance with some example embodiments.

FIG. 8 depicts an example of a process for processing a plurality of biosamples, in accordance with some example embodiments. At 810, a first sample well from a plurality of sample wells contains a biosample and one or more reagents. At 820, the plurality of sample wells are heated. At 830, an optical substrate layer coupled to the thermal layer and the sample wells distributes light from a source fiber to each of the sample wells. At 840, one or more filters coupled to the substrate layer filters light generated by the one or more reagents in response to the excitation. At 850, one or more detectors coupled to the optical substrate at the first sample well detect light emitted from the assay in the first sample well.

At 810, a first sample well such as sample well 110A may contain a biosample and one or more reagents. For example, the sample well may contain a biosample including DNA and one, two, three, or any other number of tags. The first sample well may be one of a plurality of sample wells such as sample wells 110A-110C in FIG. 1. Each sample well may include a different assay. For example, sample well 110B may contain a different biosample and/or different tags from sample well 110A. The first sample well includes a first assay.

At 820, the plurality of sample wells such as sample wells 110A-110C in FIG. 1 may be heated by a planar heater such as thermal layer 130. The planar heater may be coupled to the plurality of sample wells. For example, FIG. 1 depicts sample wells 110A-110C coupled to thermal layer 130.

At 830, an optical substrate layer such as optical substrate layer 210 in FIG. 2 may be coupled to sample wells 110A-110E. The optical substrate layer may include a source fiber such as source fiber 142 with outcouplers at the locations of the sample wells described above. One or more wavelengths of light may propagate in source fiber 142 as described above with respect to FIG. 3. Cladding may be removed and the core machined at the outcouplers in source fiber 142 as describe above. Light may be emitted at the outcouplers to provide excitation to the assays such as the first assay in the first sample well.

At 840, one or more filters coupled to the substrate layer, filter light generated by the one or more reagents in response to the excitation. For example, FIG. 6 shows filters 610A and 610B filtering light from optical substrate 210 and sample well 110A.

At 850, each sample well may have one or more associated detectors. For example, in FIG. 6 detectors 610A and 610B are associated with sample well 110A and detectors 612A and 612B are associated with sample well 110B. The detectors may be coupled to the filters such as filters 620A and 620B, and/or the detectors may be coupled to detection circuit 605. Light emitted from the reagents or tags in the first assay in the first sample well 110A may be collected by collection optics 112A, filtered by filters 620A and 620B, and provided to detectors 610A and 610B.

The subject matter described herein may be embodied in systems, apparatus, methods, and/or articles depending on the desired configuration. For example, the systems, apparatus, methods, and/or articles described herein can be implemented using one or more of the following: materials such as silica, glass, metals, or any other mechanical material, electronic components such as transistors, inductors, capacitors, resistors, and the like, a processor executing program code, an application-specific integrated circuit (ASIC), a digital signal processor (DSP), an embedded processor, a field programmable gate array (FPGA), and/or combinations thereof. These various example embodiments may include implementations in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, applications, components, program code, or code) include machine instructions for a programmable processor, and may be implemented in a high-level procedural and/or object-oriented programming language, and/or in assembly/machine language. As used herein, the term "machine-readable medium" refers to any computer program product, computer-readable medium, computer-readable storage medium, apparatus and/or device (for example, magnetic discs, optical disks, memory, Programmable Logic Devices (PLDs)) used to provide machine instructions and/or data to a programmable processor, including a machine-readable medium that receives machine instructions. In the context of this document, a "machine-readable medium" may be any non-transitory media that can contain, store, communicate, propagate or transport the instructions for use by or in connection with an instruction execution system, apparatus, or device, such as a computer or data processor circuitry. A computer-readable medium may comprise a non-transitory computer-readable storage medium that may be any media that can contain or store the instructions for use by or in connection with an instruction execution system, apparatus, or device, such as a computer. Furthermore, some of the embodiments disclosed herein include computer programs configured to cause methods as disclosed herein (see, for example, controller 150 in FIG. 1 and/or the process 800 in FIG. 8).

Although a few variations have been described in detail above, other modifications or additions are possible. In particular, further features and/or variations may be provided in addition to those set forth herein. Moreover, the example embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method of processing a plurality of biosamples, the method comprising:

providing, in each of a plurality of sample holders of a planar biosample monitoring device, a biosample and one or more reagents, wherein each sample holder includes a different assay;

heating the plurality of sample holders by a planar heater thermally coupled to the plurality of sample holders;

distributing, by an optical substrate layer optically coupled to the plurality of sample holders, light from one or more optical sources to provide excitation of the different assays, wherein the optical substrate layer includes a source fiber with outcouplers at locations corresponding to each of the sample holders;

filtering, by filters optically coupled to the optical substrate layer, light generated by a respective assay in each sample holder in response to the excitation; and detecting, by detectors optically coupled to the filters, the light generated by the respective assay in each sample holder, wherein the light from a given sample holder is detected by one or more of the detectors.

2. The method of claim 1, wherein at least one sample holder includes an assay for a polymerase chain reaction.

3. The method of claim 1, wherein the light generated by the respective assay includes luminescent light resulting from a chemical reaction.

4. The method of claim 1, wherein the light generated by the respective assay includes fluorescent light resulting from excitation of a sample in a first assay.

5. The method of claim 1, wherein the light generated by the respective assay includes phosphorescent light resulting from excitation of a sample in a first assay.

6. The method of claim 1, wherein each filter passes light of a predetermined passband and rejects light outside the predetermined passband.

7. The method of claim 1, wherein the detectors are arranged in a two-dimensional array that forms an optical detection layer of the planar biosample monitoring device.

8. The method of claim 7, wherein the planar biosample monitoring device includes diffraction gratings positioned between the optical detection layer and the optical substrate layer, and wherein each diffraction grating separates different colors of light incident thereon with little or no attenuation.

9. The method of claim 7, wherein the planar biosample monitoring device includes lenses positioned between the plurality of sample holders and the optical detection layer, and the method comprises collecting light from the plurality of sample holders and passing the collected light by the lenses to the filters.

10. The method of claim 1, wherein the detectors include a two-dimensional array of charge-coupled optical detectors, or a two-dimensional array of complementary metal oxide semiconductor optical detectors.

11. The method of claim 1, wherein the filtering of the light generated by the respective assay in each sample holder includes filtering the light over one or more ranges of wavelengths.

12. The method of claim 1, wherein the source fiber includes a cladding having a plurality of openings at a plurality of predetermined locations of the cladding of the source fiber, and distributing the light includes coupling the light to the plurality of sample holders through the plurality of openings.

* * * * *